(12) United States Patent
Cao et al.

(10) Patent No.: US 9,859,494 B1
(45) Date of Patent: Jan. 2, 2018

(54) NANOPARTICLE WITH PLURAL FUNCTIONALITIES, AND METHOD OF FORMING THE NANOPARTICLE

(71) Applicant: International Business Machines Corporation, Armonk, NY (US)

(72) Inventors: Qing Cao, Yorktown Heights, NY (US); Kangguo Cheng, Schenectady, NY (US); Zhengwen Li, Chicago, IL (US); Fei Liu, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 21 days.

(21) Appl. No.: 15/197,207

(22) Filed: Jun. 29, 2016

(51) Int. Cl.
| | |
|---|---|
| *H01L 21/31* | (2006.01) |
| *H01L 21/469* | (2006.01) |
| *H01L 21/00* | (2006.01) |
| *H01L 49/02* | (2006.01) |
| *H01L 21/02* | (2006.01) |
| *H01L 21/78* | (2006.01) |
| *A61K 9/14* | (2006.01) |

(52) U.S. Cl.
CPC .............. *H01L 49/02* (2013.01); *A61K 9/143* (2013.01); *H01L 21/0217* (2013.01); *H01L 21/02422* (2013.01); *H01L 21/02532* (2013.01); *H01L 21/02601* (2013.01); *H01L 21/7806* (2013.01)

(58) Field of Classification Search
CPC ......... H01L 49/02; H01L 21/02; H01L 21/78; H01L 21/00

USPC ................. 438/761, 763, 780; 977/700; 257/E21.01, E21.299, E21.613

See application file for complete search history.

(56) References Cited

U.S. PATENT DOCUMENTS

| | | | |
|---|---|---|---|
| 7,585,783 B2 * | 9/2009 | Nakamura ............ | H01L 21/288 257/E21.476 |
| 7,767,017 B2 | 8/2010 | Lahann et al. | |
| 7,851,294 B1 * | 12/2010 | Basco ................... | B82Y 10/00 257/202 |
| 8,052,849 B2 | 11/2011 | Lahann et al. | |
| 8,903,661 B2 | 12/2014 | Haick et al. | |
| 8,999,244 B2 | 4/2015 | Haick et al. | |
| 9,272,334 B2 | 3/2016 | Carpenter | |
| 2004/0202682 A1 | 10/2004 | Emrick et al. | |
| 2005/0170178 A1 * | 8/2005 | Chen .................... | C01F 11/185 428/402 |
| 2006/0115983 A1 * | 6/2006 | Fujii ..................... | H01L 21/288 438/640 |
| 2006/0158482 A1 * | 7/2006 | Nakamura ............ | H01L 21/288 347/45 |
| 2008/0150091 A1 * | 6/2008 | Lin ....................... | H04L 5/1423 257/635 |
| 2009/0194839 A1 * | 8/2009 | Bertin ................... | B82Y 10/00 257/476 |

(Continued)

FOREIGN PATENT DOCUMENTS

| | | |
|---|---|---|
| CN | 105147619 A | 12/2015 |
| JP | 2004-526830 A | 9/2004 |
| JP | 2004-527606 A | 9/2004 |

*Primary Examiner* — Sheikh Maruf
(74) *Attorney, Agent, or Firm* — Vazken Alexanian; McGinn IP Law Group, PLLC

(57) ABSTRACT

A nanoparticle includes a cuboid base including a semiconductor material, and a plurality of surfaces formed on the base and including a plurality of functionalities, respectively.

14 Claims, 11 Drawing Sheets

(56) References Cited

U.S. PATENT DOCUMENTS

| | | | | |
|---|---|---|---|---|
| 2009/0267225 | A1* | 10/2009 | Eguchi | H01L 21/561 257/729 |
| 2009/0317968 | A1* | 12/2009 | Nagata | H01L 27/12 438/600 |
| 2011/0042790 | A1* | 2/2011 | Lin | G03F 7/0035 257/635 |
| 2012/0080686 | A1* | 4/2012 | Mauder | H01L 21/0237 257/76 |
| 2014/0017496 | A1* | 1/2014 | Fuji | C01B 33/18 428/402 |
| 2014/0287236 | A1* | 9/2014 | Fuji | C01B 33/24 428/402 |
| 2014/0323968 | A1* | 10/2014 | Rogers | H05K 13/0023 604/113 |
| 2016/0141208 | A1* | 5/2016 | Joachim | H01L 24/03 438/114 |

* cited by examiner

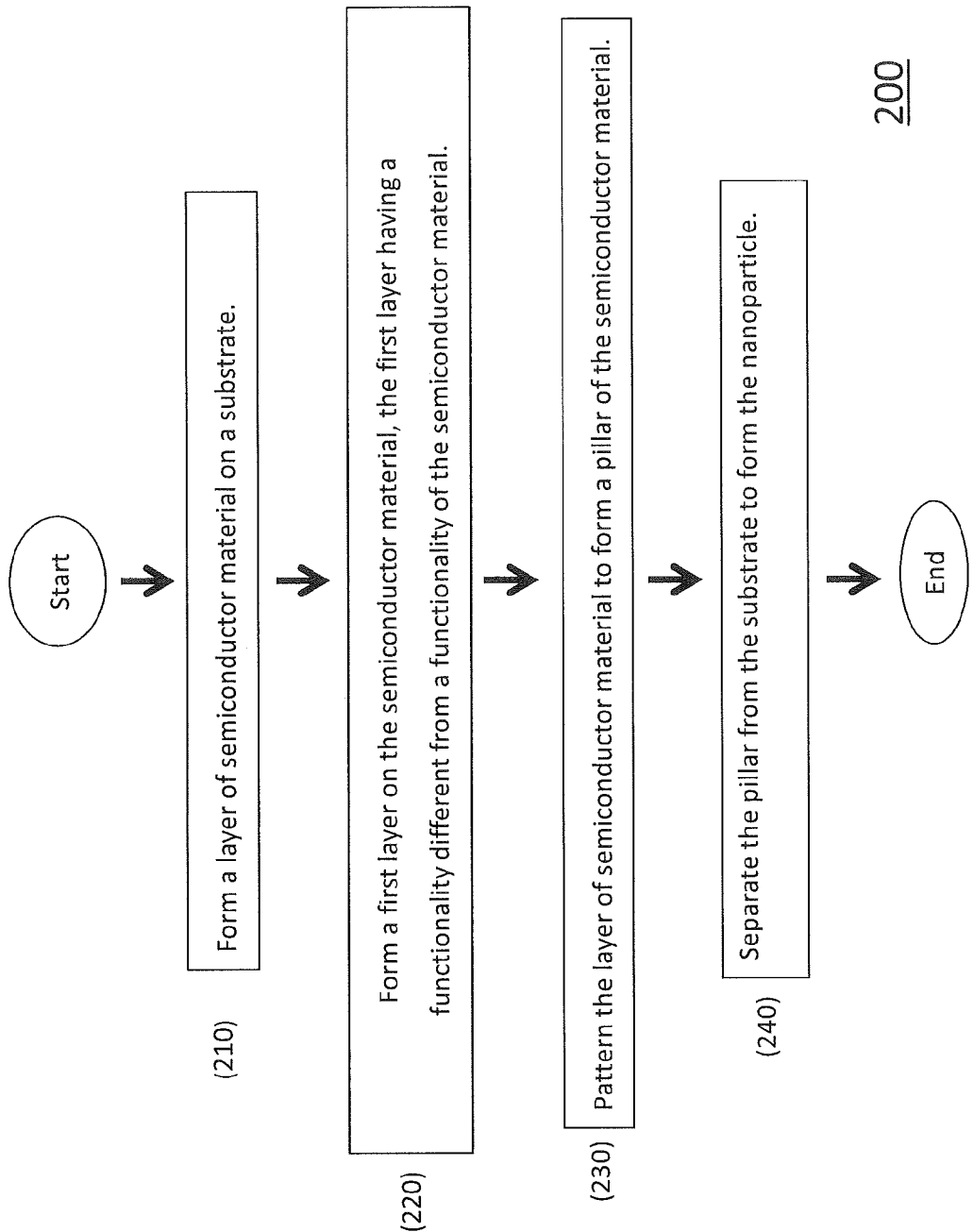

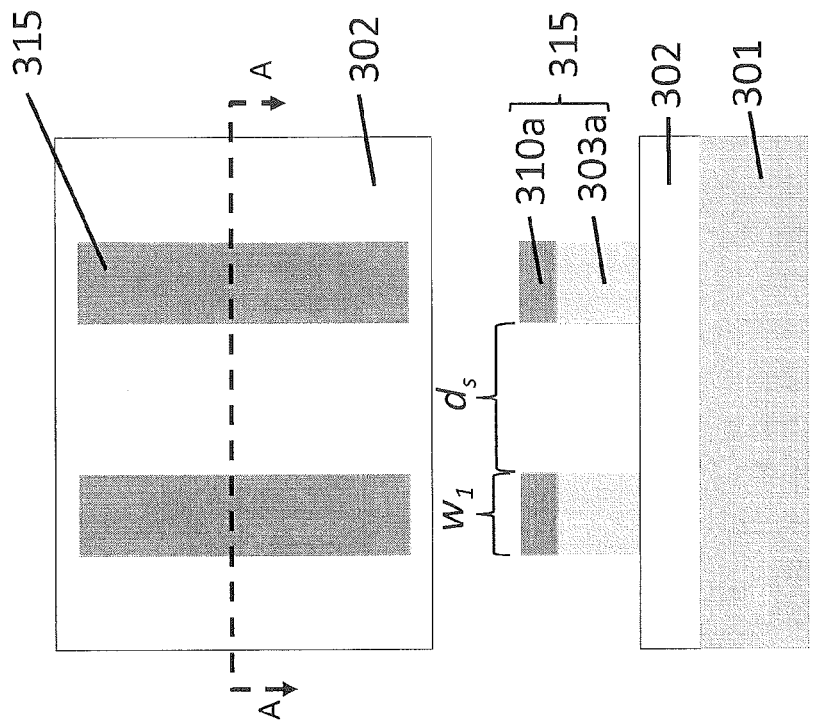
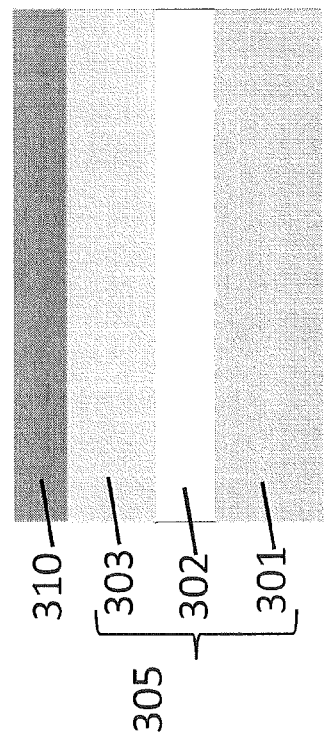
Figure 3B
Figure 3A

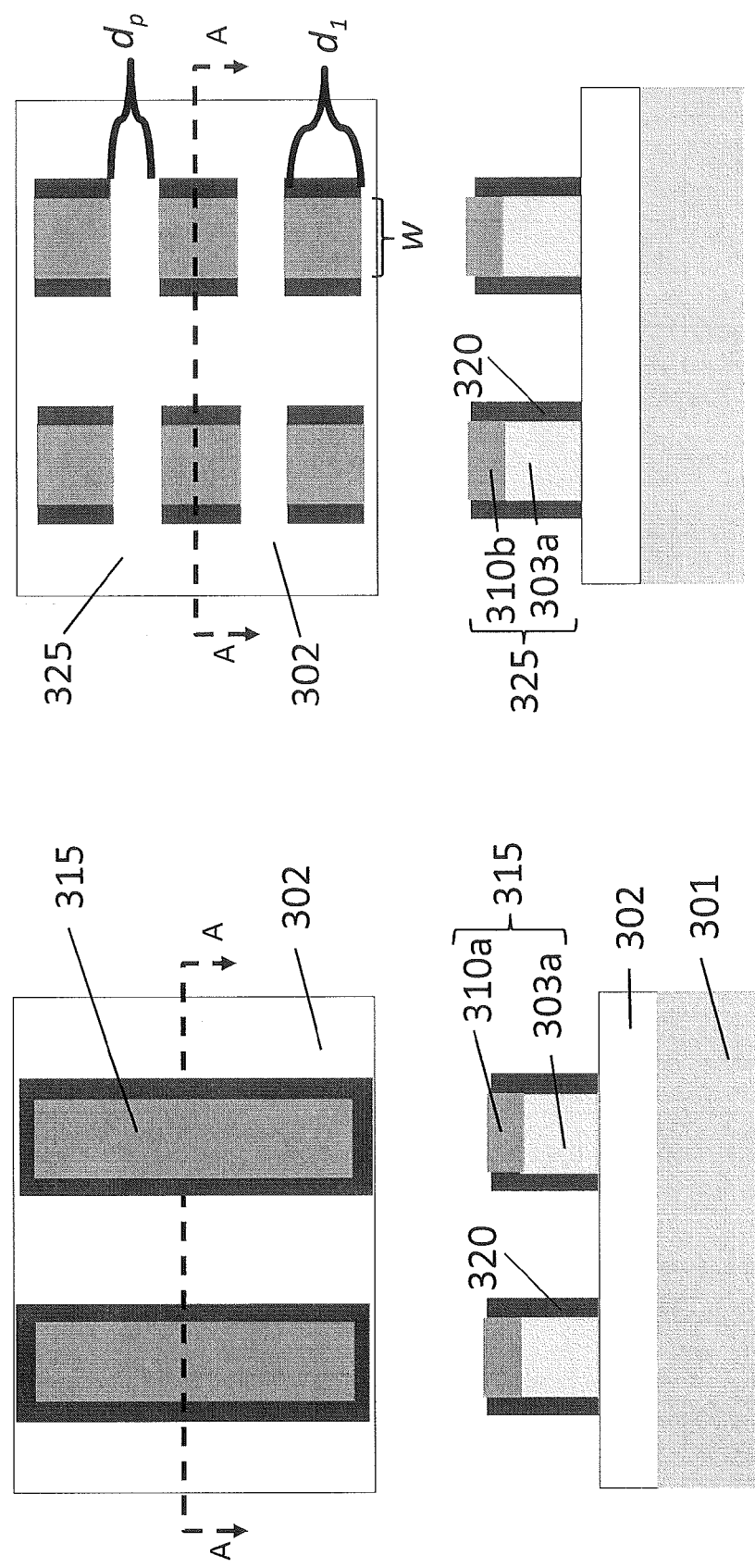

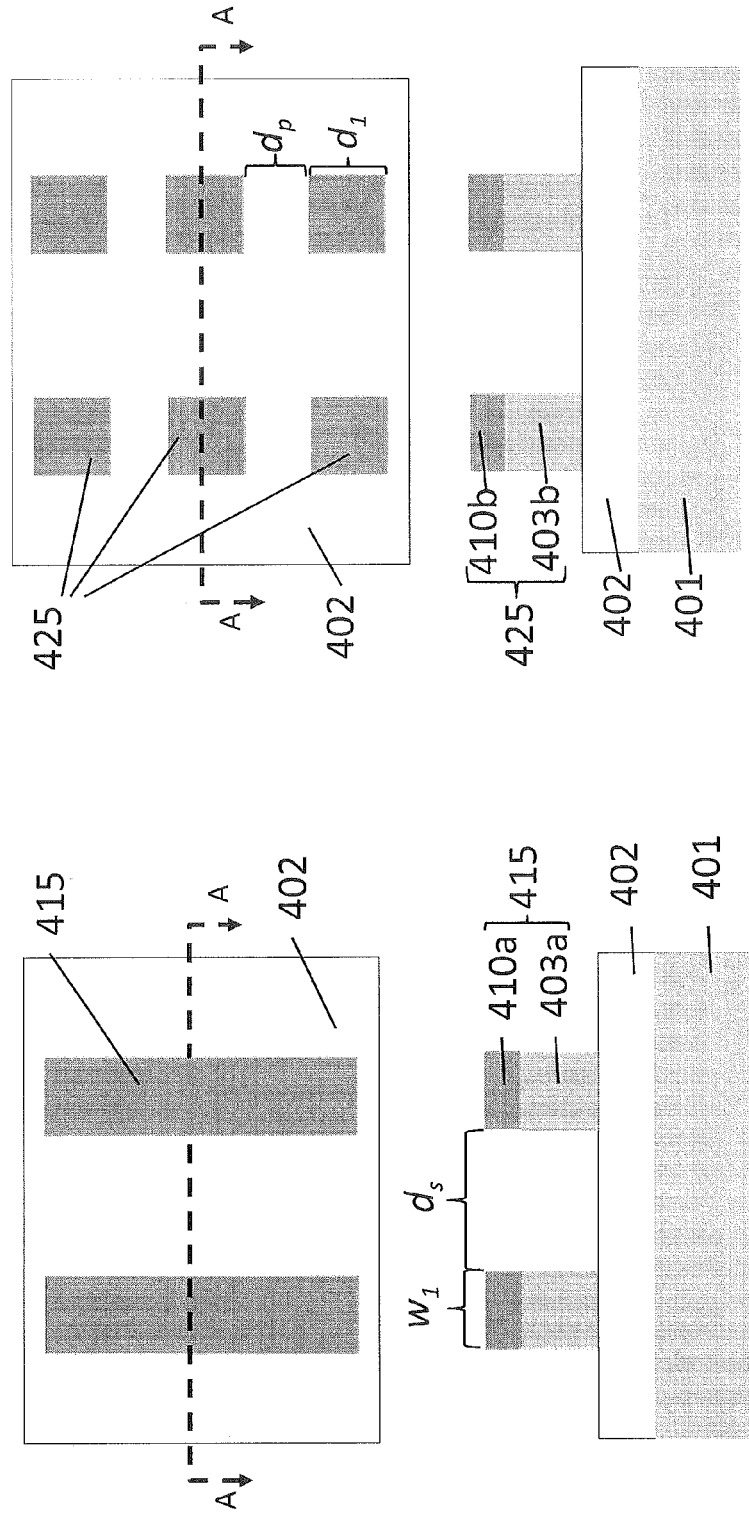

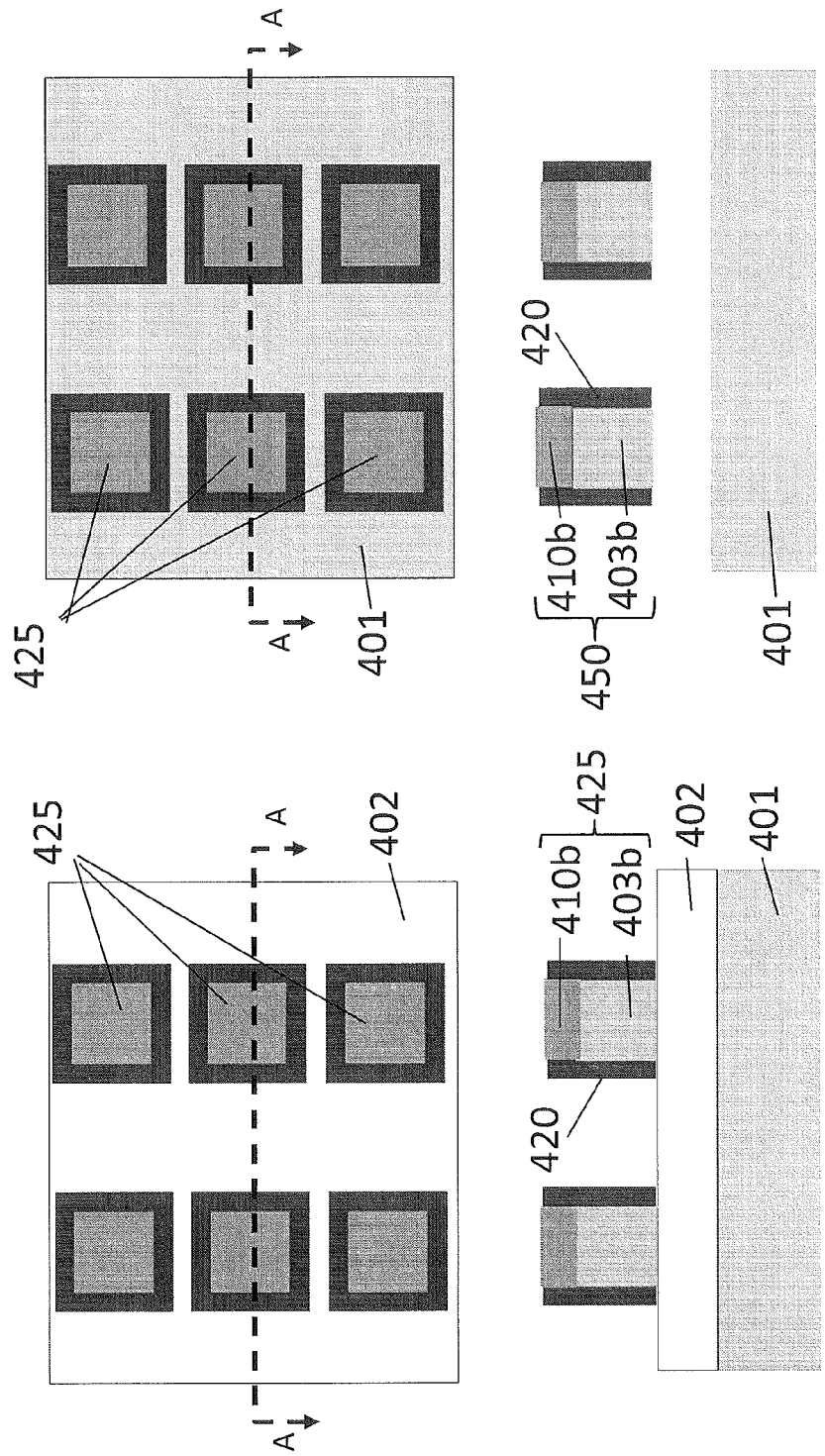

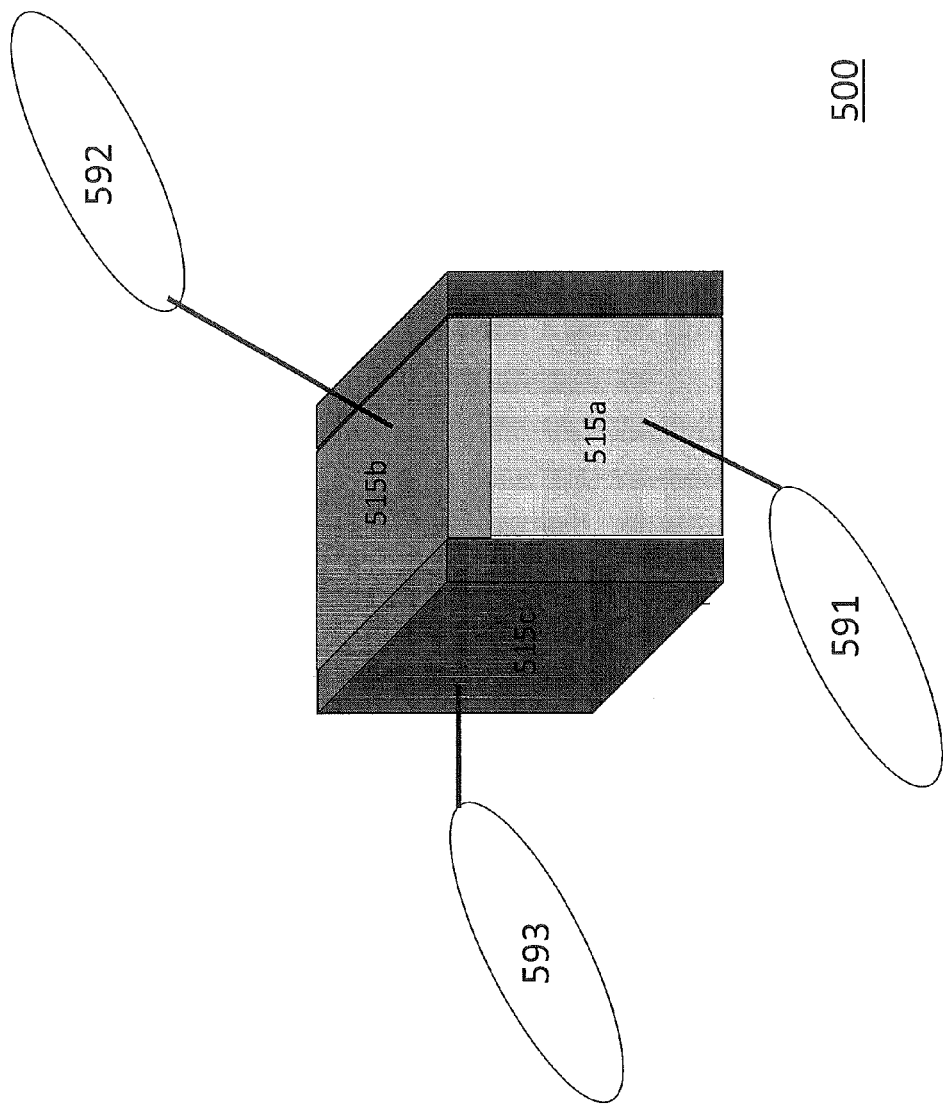

NANOPARTICLE WITH PLURAL FUNCTIONALITIES, AND METHOD OF FORMING THE NANOPARTICLE

BACKGROUND OF THE INVENTION

Field of the Invention

The present invention relates to a nanoparticle and a method of forming the nanoparticle, and more particularly, to a nanoparticle which includes a cuboid base including a semiconductor material.

Description of the Related Art

There are special types of nanoparticles (e.g., Janus particles) having surfaces with two or more distinct physical properties. The unique surface of these nanoparticles allows different types of chemistry to occur on the same particle.

The particles can be used as sensors, where toposelective functionalization of the hemispheres for (bio)-chemical targeting enables such particles to interact with receptors on surfaces or in solution, which translates into different rotational properties that can be used for detection purposes.

The particles can also be used, for example, in E-ink display. Microspheres died black and white with carbon black and titania pigments can be actuated by reverting AC-electrical fields when transparent electrodes are sandwiched on top and below a monolayer of these particles.

Another very promising application is to utilize the multiple functions of the particles to achieve targets including the rapid and sensitive detection of pathogens, specific cell labeling, in vitro and in vivo imaging, and the targeted delivery and on demand release of pharmaceuticals in site-specific treatments of injuries or diseases at the same time.

The particles can be fabricated, for example, via simple masking, self assembly, or phase separation.

However, it is still a daunting challenge to make the particles with highly uniform size and multiple (more than two) faces with different functionalities or properties.

SUMMARY

In view of the foregoing and other problems, disadvantages, and drawbacks of the aforementioned conventional devices and methods, an exemplary aspect of the present invention is directed to a nanoparticle and a method of forming a nanoparticle, which may provide a more uniform nanoparticle than in conventional nanoparticles and methods of forming nanoparticles.

An exemplary aspect of the present invention is directed to a nanoparticle including a cuboid base including a semiconductor material, and a plurality of surfaces formed on the base and including a plurality of functionalities, respectively.

Another exemplary aspect of the present invention is directed to a method of forming a nanoparticle, the method includes forming a layer of semiconductor material on a substrate, forming a first layer on the semiconductor material, the first layer having a functionality different from a functionality of the semiconductor material, patterning the layer of semiconductor material to form a pillar of the semiconductor material, and separating the pillar from the substrate to form the nanoparticle.

Another exemplary aspect of the present invention is directed to a method of forming a nanoparticle, including forming a layer of semiconductor material on a buried oxide layer of a semiconductor-on-insulator (SOI) substrate, forming a first layer on the semiconductor material, the first layer having a functionality different from a functionality of the semiconductor material, patterning the layer of semiconductor material to form a pillar of the semiconductor material, the patterning of the layer of semiconductor material including a first etch to form a plurality of strips of the semiconductor material, and a second etch to divide the plurality of strips into a plurality of pillars of the semiconductor material, and etching the buried oxide layer to separate the pillar from the buried oxide layer to form the nanoparticle.

With its unique and novel features, the present invention provides a nanoparticle and a method of forming a nanoparticle, which may provide a more uniform nanoparticle than in conventional nanoparticles and methods of forming nanoparticles.

BRIEF DESCRIPTION OF THE DRAWINGS

The foregoing and other objects, aspects and advantages will be better understood from the following detailed description of the embodiments of the invention with reference to the drawings, in which:

FIG. 2 illustrates a method 200 of forming a nanoparticle (e.g., the nanoparticle 100), according to an exemplary aspect of the present invention;

FIG. 3A illustrates a semiconductor-on-insulator (SOI) substrate 305 that may be used in the method 300, according to an exemplary aspect of the present invention;

FIG. 3B illustrates a patterning of the silicon layer 303 and the insulator layer 310 (e.g., by sidewall imaging transfer (SIT) technique), according to an exemplary aspect of the present invention;

FIG. 3C illustrates forming a conductor (e.g., metal) layer 320 on a sidewall (e.g., opposing sidewalls) of the strips 315, according to an exemplary aspect of the present invention;

FIG. 3D illustrates dividing the strips 315 to transform a strip 315 of the plurality of strips 315 into a plurality of pillars 325 which include the silicon layer 303b and the insulator layer 310b, according to an exemplary aspect of the present invention;

FIG. 4B illustrates patterning of the silicon layer 403 and the insulator layer 410 (e.g., by etching) to form a plurality of strips 415 including the silicon layer 403a and the insulator layer 410a, according to an exemplary aspect of the present invention;

FIG. 4C illustrates a dividing of the strips 415 to transform a strip 415 of the plurality of strips 415 into a plurality of pillars 425, according to an exemplary aspect of the present invention;

FIG. 4D illustrates a forming of a conductor (e.g., metal) layer 420 on a sidewall (e.g., on each of the four sidewalls) of the pillars 425, according to an exemplary aspect of the present invention;

FIG. 4E illustrates a separating (e.g., releasing) of the plurality of pillars 425 from the BOX layer 402, so that the pillars 425 become nanoparticles 450 which include the silicon layer 403b, the insulator layer 410b and the conductor layer 420, according to an exemplary aspect of the present invention.

FIG. 5 illustrates a pharmaceutical 500 (e.g., a polyfunctional pharmaceutical) including a nanoparticle 550 (e.g., nanoparticle 100), according to an exemplary aspect of the present invention.

DETAILED DESCRIPTION OF THE EXEMPLARY EMBODIMENTS OF THE INVENTION

Figure 1:
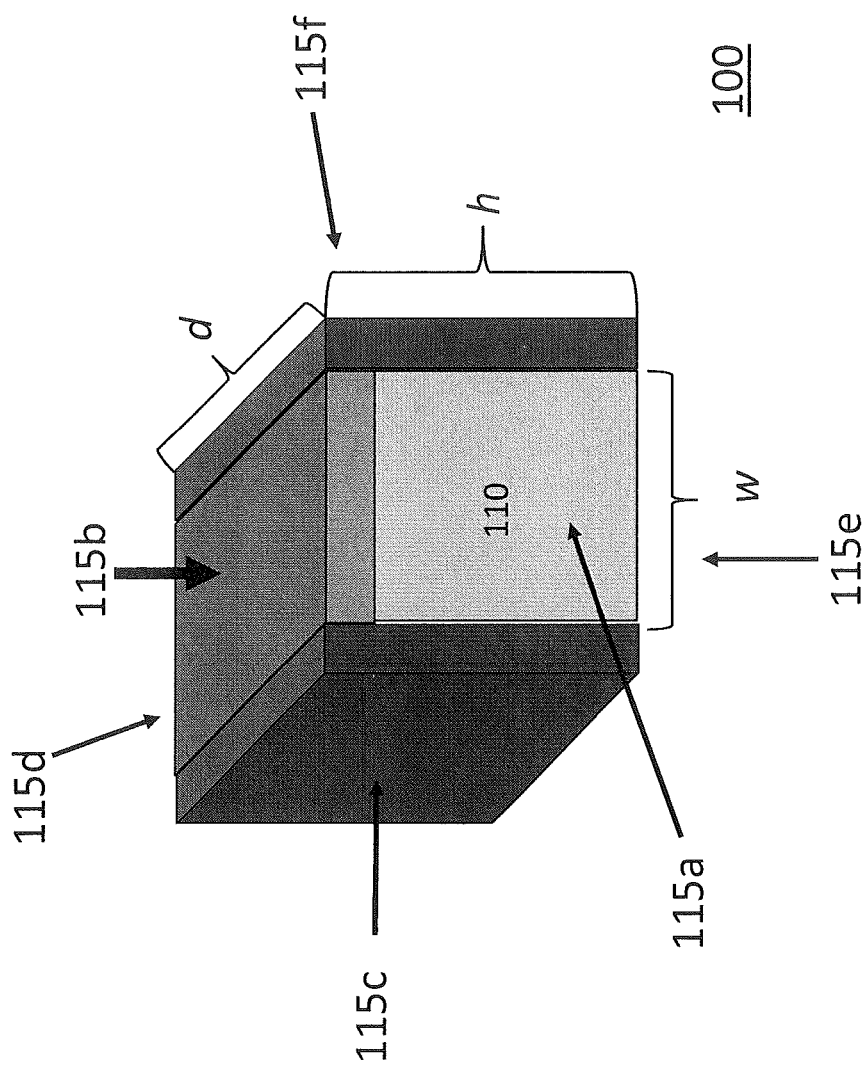
FIG. 1 illustrates a nanoparticle 100 according to an exemplary aspect of the present invention.

Referring now to the drawings, FIGS. 1-11 illustrate the exemplary aspects of the present invention.

As noted above, conventionally it is difficult to form nanoparticles (e.g., Janus particles) with highly uniform size and multiple (more than two) faces with different functionalities or properties. However, the exemplary aspects of the present invention may provide a method and structure for forming uniform nanoparticles. That is, the exemplary aspects of the present invention may provide a method and structure for forming uniform nanoparticles, each nanoparticle having multiple planes that have different properties (e.g., functions).

In addition, conventional methods of forming nanoparticles may cause damage to a first surface of the nanoparticle, while attempting to functionalize a second surface of the nanoparticle. However, the exemplary aspects of the present invention may provide a method of forming nanoparticles.

FIG. 1 illustrates a nanoparticle 100 according to an exemplary aspect of the present invention, without damaging one surface of the nanoparticle while attempting to functionalize another surface of the nanoparticle.

As illustrated in FIG. 1, the nanoparticle 100 includes a cuboid base 110 including a semiconductor material, and a plurality of surfaces 115a-f formed on the base and including a plurality of functionalities, respectively. The plurality of surfaces may include a plurality of faces of the cuboid base. Thus, for example, the plurality of functionalities may include a first functionality formed on a first face of the plurality of faces, a second functionality different from the first functionality formed on a second face of the plurality of faces, and so on.

The surfaces of the cuboid base (e.g., the faces of the cuboid base) may be different in one or more properties (e.g., functions). For example, the surfaces may be different in a bonding property. That is, a first surface of the cuboid base may form a strong bond with a material, whereas a second surface of the cuboid base may not form a strong bond with the material. As another example, the first surface of the cuboid base may form a bond with a material that is easily broken under a predetermined condition (e.g., radiation, acidic condition, presence of enzymes, etc.), whereas, the second surface of the cuboid base may form a bond with the material which is not easily broken under the predetermined condition.

As another example, the surfaces may be different in an energy absorption property. That is, a first surface of the cuboid base may absorb a high amount of energy (e.g., thermal energy) from a radiation source, whereas a second surface of the cuboid base may not absorb a high amount of energy transmitted to the nanoparticle from an energy source (e.g., thermal energy from a radiation source). Alternatively, the first surface of the cuboid base may be easily removed (e.g., dissolved) by the energy, whereas a second surface of the cuboid base may be impervious to the energy.

As another example, the surfaces may be different in a biodegradability property (i.e., the ease with which the surface is decomposed by bacteria or other biological means). That is, a first surface of the cuboid base may have a high biodegradability (i.e., easily decomposed), whereas a second surface of the cuboid base may have a low biodegradability (i.e., easily decomposed).

Referring again to FIG. 1, the cuboid base 110 of the nanoparticle 100 is illustrated as being a cube where all of the sides have an equal length (i.e., w=h=d). However, the cuboid base 110 is not limited to being a cube. That is, the sides of the cuboid base 110 may have unequal lengths, so that the faces of the cuboid base 110 may have a rectangular shape instead of a square shape, and the cuboid base 110 has the shape of a rectangular cuboid, instead of a square cuboid.

For example, in an exemplary embodiment, the cuboid base 110 includes silicon (e.g., is formed entirely of silicon). The cuboid base 110 may alternatively include other semiconductor materials, such as germanium, silicon germanium, a group III-V semiconductor material such as GaN, GaInN, GaAlN, GaAs, a group II-VI semiconductor material such ZnSe, ZnTe, ZnCdSe, ZnCdSeTe, and so on.

In this exemplary embodiment, the surface 115a may be formed of an exposed surface of the cuboid base 110. That is, no other material is formed on this side of the cuboid base 110, so that the surface 115a of the nanoparticle is formed of a surface of the cuboid base 110. Thus, the surface 115a may include the semiconductor material of the cuboid base 110 (e.g., germanium, silicon germanium, a group III-V semiconductor material such as GaN, GaInN, GaAlN, GaAs, a group II-VI semiconductor material such ZnSe, ZnTe, ZnCdSe, ZnCdSeTe, and so on).

In this exemplary embodiment, the surface 115b includes an insulator layer. The insulator layer may include, for example, one or more electrically insulating materials such as silicon nitride, silicon oxide, and so on.

The surface 115c may include a conductive layer such as a metal layer. The conductor layer may include, for example, a metal such as gold, tungsten, a metal alloy, and so on. The conductor layer may alternatively include polysilicon or other non-metal conductor.

The lengths of the sides of the cuboid base 110 (e.g., w, h, d) may be in a range, for example, of 2 nm to 50 nm. Further, the thicknesses of the layers formed on the surfaces of the cuboid base 110 (e.g., the thickness of the silicon nitride layer forming the surface 115b, the thickness of the gold layer forming the surface 115c, and so on) may be in a range, for example, of 0.5 nm to 10 nm.

Further, the lengths of the sides of the cuboid base 110 (e.g., w, h, d) may be varied in order to vary the relative amount of surface area for each of the surfaces 115a-f, and therefore, vary the proportionate functionalities of the nanoparticle 100. For example, the length h may be increased (while holding the lengths w and d constant) in order to increase the ratio of functionality for surface 115c (e.g., gold) with respect to the functionality of surface 115b (e.g., silicon nitride), and so on.

In addition, a thickness of the layers formed on the surfaces of the cuboid base 110 may be varied in order to vary the proportionate functionalities of the nanoparticle 100. For example, the thickness of the gold layer (surface 115c) may be increased (while holding the thickness of the insulator layer (surface 115b) constant in order to increase the ratio of functionality for surface 115c (e.g., gold) with respect to the functionality of surface 115b (e.g., silicon nitride), and so on.

Referring again to the drawings, FIG. 2 illustrates a method 200 of forming a nanoparticle (e.g., the nanoparticle 100), according to an exemplary aspect of the present invention.

As illustrated in FIG. 2, the method 200 includes forming (210) a layer of semiconductor material (e.g., a silicon layer, germanium layer, GaN layer, etc.) on a substrate, forming (220) a first layer (e.g., a silicon nitride layer) on the semiconductor material, the first layer having a functionality different from a functionality of the semiconductor material, patterning (230) (e.g., by etching such as reactive ion etching (RIE) the layer of semiconductor material to form a pillar of the semiconductor material, and separating (240) the pillar from the substrate (e.g., undercutting the pillar using, for example, hydrofluoric acid) to form the nanoparticle.

For example, the substrate may include a semiconductor-on-insulator (SOI) substrate including a buried oxide layer, and the layer of semiconductor material is formed on the buried oxide layer. In this case, the separating of the pillar from the substrate may include undercutting the buried oxide layer by etching the buried oxide layer.

Further, the patterning of the layer of semiconductor material may include a first etch to form a plurality of strips of the semiconductor material, and a second etch to divide the plurality of strips into a plurality of pillars of the semiconductor material.

Further, the method 200 may also include forming a second layer (e.g., a gold layer, a tungsten layer, etc.) on the semiconductor material, the second layer having a functionality different from the functionality of the semiconductor material, and different from the functionality of the first layer. In this case, the forming of the second layer is performed between the first etch and the second etch, so that the second layer is formed on two faces of the nanoparticle, or after the second etch, so that the second layer is formed on four faces of the nanoparticle.

FIGS. 3A-3F illustrate a method 300 of forming a nanoparticle 350 (e.g., the nanoparticle 100), according to another exemplary aspect of the present invention.

In particular, FIG. 3A illustrates a semiconductor-on-insulator (SOI) substrate 305 that may be used in the method 300, according to an exemplary aspect of the present invention. The SOI substrate 305 includes a substrate 301 (e.g., silicon), a buried insulator layer 302 (e.g., buried oxide layer (BOX)) formed on the substrate 301, and a semiconductor layer 303 (e.g., silicon layer) formed on the BOX layer 302. Further, an insulator layer 310 (e.g., silicon nitride) (e.g., cap layer) is formed on the silicon layer 303.

FIG. 3B illustrates a patterning of the silicon layer 303 and the insulator layer 310 (e.g., by sidewall imaging transfer (SIT) technique), according to an exemplary aspect of the present invention. The SIT process enables forming strips with well-controlled dimensions) to form a plurality of strips 315 including the silicon layer 303a and the insulator layer 310a. In particular, a top portion of FIG. 3B provides a topdown view (e.g., plan view), and a bottom portion of FIG. 3B provides a cross-sectional view of the device along A-A after the patterning is performed.

The width $w_1$ of the strips 315 should be substantially equal to the desired width of the cuboid base 110 of the nanoparticles (e.g., w in FIG. 1). That is, the width $w_1$ should be in a range from 2 nm to 50 nm. The distance $d_s$ between the strips 315 may be in a range from 5 nm to 100 nm.

FIG. 3C illustrates forming a conductor (e.g., metal) layer 320 on a sidewall (e.g., opposing sidewalls) of the strips 315, according to an exemplary aspect of the present invention. That is, the conductor layer 320 is formed on a sidewall of the silicon layer 303a and the insulator layer 310a. In particular, a top portion of FIG. 3C provides a topdown view (e.g., plan view), and a bottom portion of FIG. 3C provides a cross-sectional view of the device along A-A after the conductor layer 320 is formed.

The conductor layer 320 may be formed, for example, by depositing the conductor (e.g., metal) over the entire surface of the structure (e.g., on the surface of the BOX layer 302, on the surface of the insulator layer 310a, etc.), and then etching (e.g., by RIE) the conductor so that the conductor layer 320 remains on the sidewall of the strips 315.

The thickness of the conductor layer 320 should be substantially equal to the desired thickness of the conductor layer of the nanoparticles (e.g., the thickness of the conductor layer forming the surface 115c in FIG. 1). That is, the thickness should be in a range from 0.5 nm to 10 nm.

FIG. 3D illustrates dividing the strips 315 to transform a strip 315 of the plurality of strips 315 into a plurality of pillars 325 which include the silicon layer 303b and the insulator layer 310b, according to an exemplary aspect of the present invention. In particular, a top portion of FIG. 3D provides a topdown view (e.g., plan view), and a bottom portion of FIG. 3D provides cross-sectional view of the device along A-A after the dividing is performed. The division of a strip can be done by the SIT process. Other patterning technique can also be used.

The dividing of the strips 315 may be performed by patterning (e.g., using a mask layer to pattern) the strips 315. The patterning should be performed so that the length $d_1$ of the pillar 325 is substantially equal to the desired length d of the cuboid base 110. The distance $d_p$ between the pillars 325 formed from a strip 325 may be in a range from 5 nm to 100 nm.

In particular, the distance $d_s$ between the strips 315, and the distance $d_p$ between the pillars 325 should be long enough to permit for separating the pillars 325 from the BOX layer 302 in a later step.

Figure 3E:
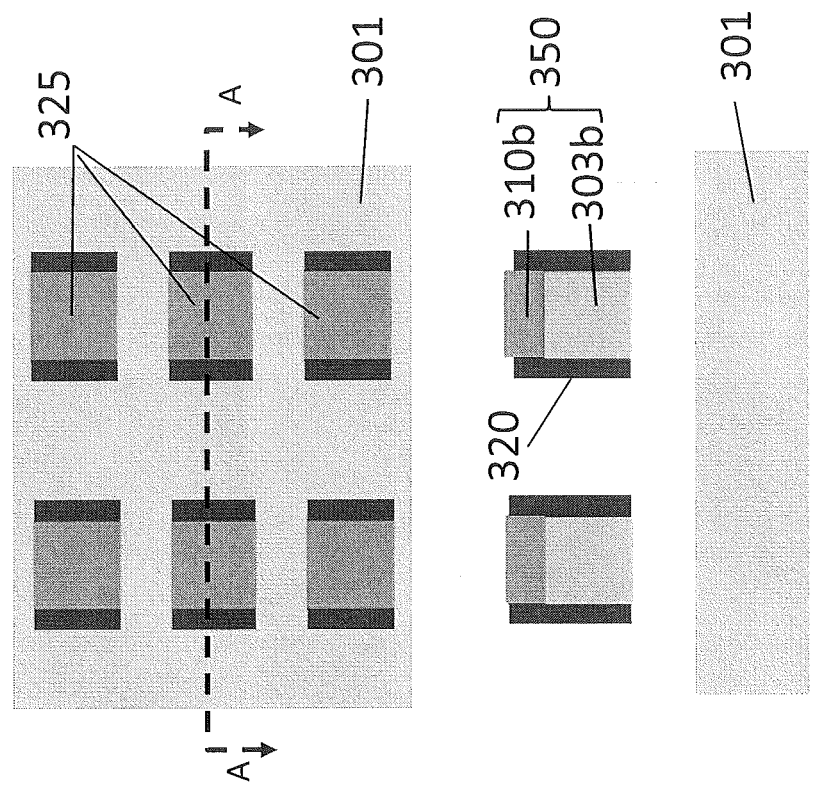
FIG. 3E illustrates a separating (e.g., releasing) of the plurality of pillars 325 from the BOX layer 302, according to an exemplary aspect of the present invention.

FIG. 3E illustrates a separating (e.g., releasing) of the plurality of pillars 325 from the BOX layer 302, according to an exemplary aspect of the present invention. As illustrated in FIG. 3E, the pillars 325 are separated and become nanoparticles 350 including the silicon layer 303b as a cuboid base (e.g., cuboid base 110 in FIG. 1), the insulator layer 310b and the conductor layer 320. In particular, a top portion of FIG. 3E provides a topdown view (e.g., plan view), and a bottom portion of FIG. 3E provides a cross-sectional view of the device along A-A after the pillars 325 are separated from the BOX layer 302.

The plurality of pillars 325 may be separated from the BOX layer 302, for example, by performing an etch to undercut the BOX layer 302.

The result of the method 300 is a plurality of nanoparticles 350 having a structure which is similar to the structure of the nanoparticle 100 in FIG. 1. That is, the nanoparticles 350 formed by the method 300 may include a cuboid base which is formed of silicon (e.g., formed entirely of silicon), and the six surfaces on the cuboid base have different properties. Namely, one surface includes the insulator layer 310b, two surfaces include the conductor layer 320, and three surfaces include the silicon layer 303b.

Further, the plurality of nanoparticles 350 formed by the method 300 may be substantially uniform in dimension, and thus, uniform in overall functionality.

In an exemplary aspect of the present invention, a superior uniformity may achieved thanks to the well-controlled semiconductor patterning techniques such as sidewall imaging transfer and deposition. In particular, the deviation among a size (e.g., height, depth, width) of the nanoparticles may be less than 10%., and a deviation in a thickness of the layers may be no greater than 10%

It should be noted that, although silicon is used as the material of the cuboid base in the method 300, other semiconductor materials (e.g., germanium, GaN, etc.) may be used instead of silicon.

FIGS. 4A-4E illustrate a method 400 of forming a nanoparticle 450 according to another exemplary aspect of the present invention.

Figure 4A:
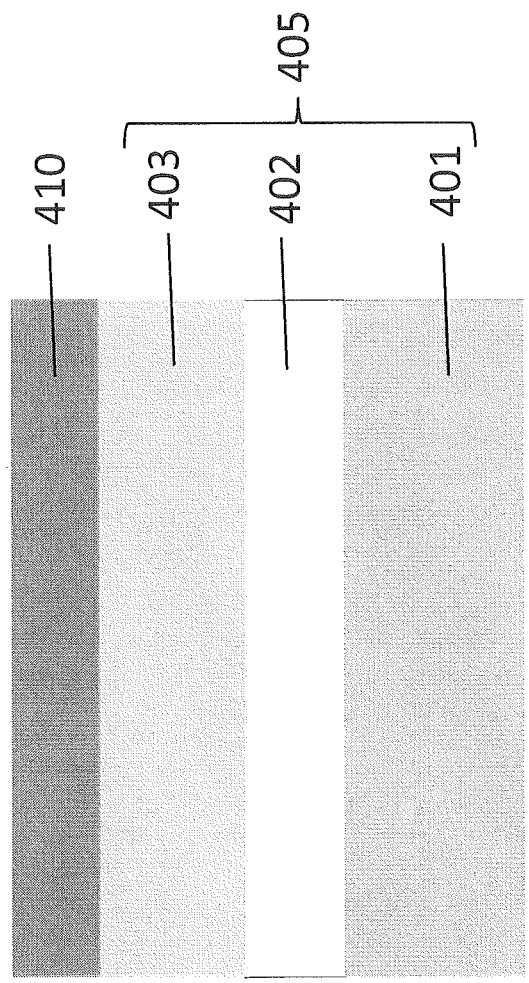
FIG. 4A illustrates a semiconductor-on-insulator (SOI) substrate 405 (e.g., similar to FIG. 3A) that may be used in the method 400, according to an exemplary aspect of the present invention.

In particular, FIG. 4A illustrates a semiconductor-on-insulator (SOI) substrate 405 (e.g., similar to FIG. 3A) that may be used in the method 400, according to an exemplary aspect of the present invention. The SOI substrate 405 includes a substrate 401 (e.g., silicon), a buried oxide layer (BOX) 402 formed on the substrate 401, and a silicon layer 403 formed on the BOX layer 402. Further, an insulator layer 410 (e.g., silicon nitride) (e.g., cap layer) is formed on the silicon layer 403.

FIG. 4B illustrates patterning of the silicon layer 403 and the insulator layer 410 (e.g., by etching) to form a plurality of strips 415 including the silicon layer 403a and the insulator layer 410a, according to an exemplary aspect of the present invention. In particular, a top portion of FIG. 4B provides a topdown view (e.g., plan view), and a bottom portion of FIG. 4B provides a cross-sectional view of the device along A-A after the patterning is performed.

The width $w_1$ of the strips 415 should be substantially equal to the desired width of the cuboid base 110 of the nanoparticles (e.g., w in FIG. 1). That is, the width $w_1$ should be in a range from 2 nm to 50 nm. The distance $d_s$ between the strips 415 may be in a range from 5 nm to 100 nm.

FIG. 4C illustrates a dividing of the strips 415 to transform a strip 415 of the plurality of strips 415 into a plurality of pillars 425, according to an exemplary aspect of the present invention. In particular, a top portion of FIG. 4C provides a topdown view (e.g., plan view), and a bottom portion of FIG. 4C provides a cross-sectional view of the device along A-A after the dividing is performed.

That is, unlike the method 300, in the method 400, the strips 415 are divided into the pillars 425 without the formation of a conductor layer 420 on a sidewall of the strips 415.

The dividing of the strips 415 may be performed by patterning (e.g., using a mask layer to pattern) the strips 415. The patterning should be performed so that the length $d_1$ of the pillar 425 is substantially equal to the desired length d of the cuboid base. The distance $d_p$ between the pillars 425 formed from a strip 425 may be in a range from 5 nm to 100 nm.

In particular, the distance $d_s$ between the strips 415, and the distance $d_p$ between the pillars 425 should be long enough to permit for separating the pillars 425 from the BOX layer 402 in a later step.

FIG. 4D illustrates a forming of a conductor (e.g., metal) layer 420 on a sidewall (e.g., on each of the four sidewalls) of the pillars 425, according to an exemplary aspect of the present invention. That is, the conductor layer 420 is formed on a sidewall of the silicon layer 403b and the insulator layer 410b in the pillar 425. In particular, a top portion of FIG. 4D provides a topdown view (e.g., plan view), and a bottom portion of FIG. 4D provides a cross-sectional view of the device along A-A after the conductor layer 420 is formed.

The conductor layer 420 may be formed, for example, by depositing the conductor (e.g., metal) over the entire surface of the structure (e.g., on the surface of the BOX layer 402, the surface of the insulator layer 410b, etc.), and then etching (e.g., by RIE) the conductor so that the conductor layer 420 remains on the sidewall of the pillars 425.

The thickness of the conductor layer 420 should be substantially equal to the desired thickness of the conductor layer of the nanoparticles (e.g., the thickness of the conductor layer forming the surface 115c in FIG. 1). That is, the thickness should be in a range from 0.5 nm to 10 nm.

FIG. 4E illustrates a separating (e.g., releasing) of the plurality of pillars 425 from the BOX layer 402, so that the pillars 425 become nanoparticles 450 which include the silicon layer 403b, the insulator layer 410b and the conductor layer 420, according to an exemplary aspect of the present invention. In particular, a top portion of FIG. 4E provides a topdown view (e.g., plan view), and a bottom portion of FIG. 4E provides a cross-sectional view of the device along A-A after the pillars 425 are separated from the BOX layer 402.

The plurality of pillars 425 may be separated from the BOX layer 402, for example, by performing an etch to undercut the BOX layer 402.

Figure 4F:
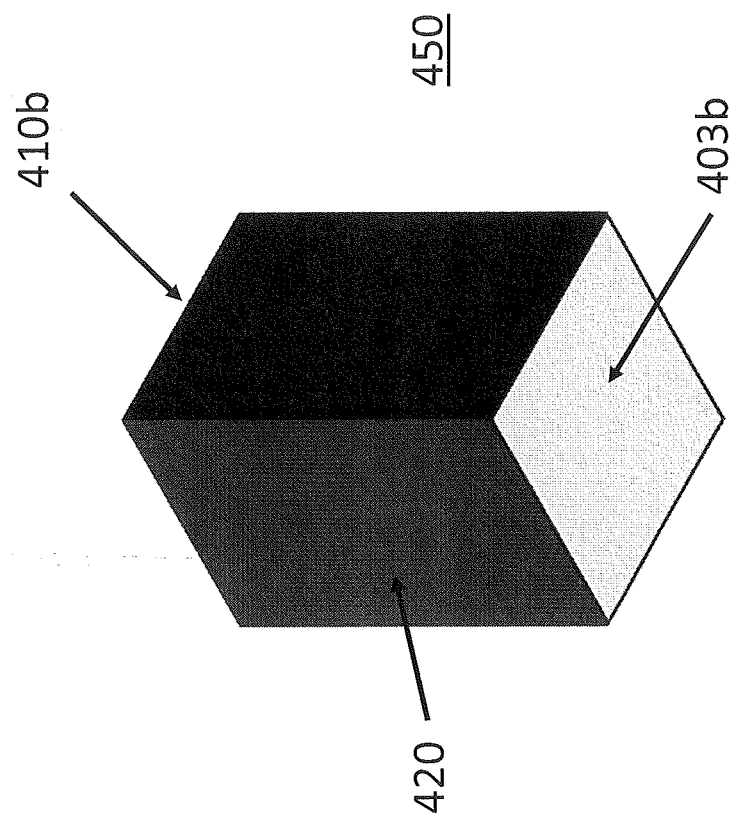
FIG. 4F illustrates the nanoparticle 450 which is formed by the method 400, according to an exemplary aspect of the present invention.

FIG. 4F illustrates the nanoparticle 450 which is formed by the method 400, according to an exemplary aspect of the present invention.

As illustrated in FIG. 4F, the result of the method 400 is a nanoparticle 450 having a structure which is different from the structure of the nanoparticle 100 in FIG. 1. That is, the nanoparticles 450 formed by the method 400 may include one surface (not visible in FIG. 4F) which includes the insulator layer 410b, four surfaces which include the conductor layer 420, and one surface which includes the silicon layer 403b (e.g., the surface which was separated from the BOX layer 402).

Further, the plurality of nanoparticles 450 formed by the method 400 may be substantially uniform in dimension, and thus, uniform in overall functionality.

It should be noted that, although silicon is used as the material of the cuboid base in the method 400, other semiconductor materials (e.g., germanium, GaN, etc.) may be used instead of silicon.

Referring again to the drawings, FIG. 5 illustrates a pharmaceutical 500 (e.g., a polyfunctional pharmaceutical) including a nanoparticle 550 (e.g., nanoparticle 100), according to an exemplary aspect of the present invention. It should be noted that although the nanoparticle 550 is similar in structure to the nanoparticle 100 in FIG. 1, the nanoparticle 550 is not limited to such a structure but may have another structure, such as the structure of nanoparticle 450 in FIG. 4F.

Similar to the nanoparticle 100, the nanoparticle 550 includes a surface 515a formed of semiconductor material (e.g., silicon), a surface 515b formed of an insulator layer, and a surface 515c formed of a conductor layer. These surfaces 515a-515c can bond to different biomaterials so that multiple biomaterials (e.g., multiple drugs) can be delivered by the pharmaceutical 500.

The pharmaceutical 500 may be ingested by a patient (e.g., human patient, animal patient, etc.). As illustrated in FIG. 5, the pharmaceutical 500 includes a first biomaterial (e.g., drug) 591 which is bonded to the surface 515a, a second biomaterial (e.g., drug) 592 which is bonded to the surface 515b, and a third biomaterial (e.g., drug) 593 which is bonded to the surface 515c. For example, the first biomaterial 591 may be an antibiotic, the second biomaterial 592 may be an analgesic, and the third biomaterial 593 may be a fever reducer.

Figure 6:
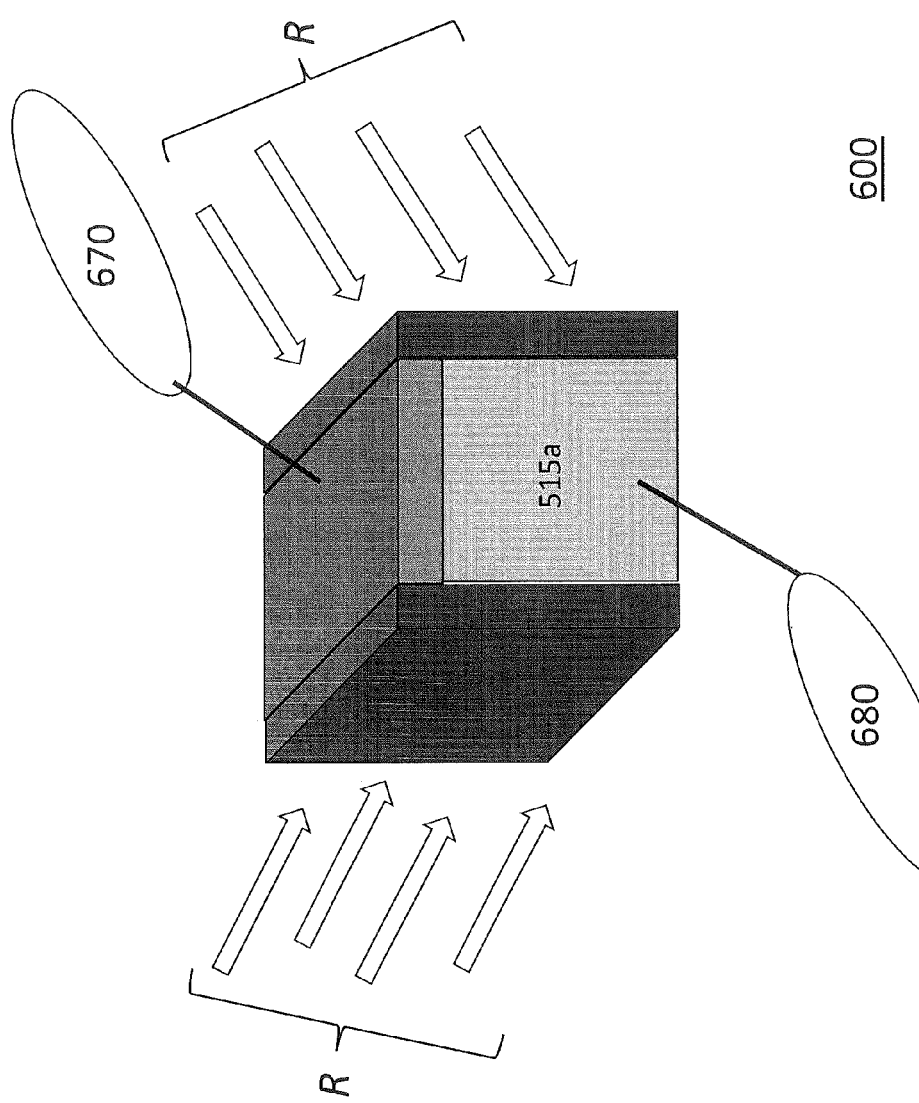
FIG. 6 illustrates a pharmaceutical 600, according to another exemplary aspect of the present invention.

FIG. 6 illustrates a pharmaceutical 600, according to another exemplary aspect of the present invention. The pharmaceutical 600 may include the nanoparticle 550, and may be used for locally controlled imaging and multiple drug releases for more precise medical treatments.

For example, the surface 515c in the pharmaceutical 600 may include gold surface (e.g., a gold layer). When an energy source such as a laser producing non-ionising electromagnetic radiation R is applied, conversion to heat energy occurs in Au nanoparticles owing to electron excitation and relaxation. Furthermore, lasers can be specifically tuned to the surface plasmon resonance frequency of the Au. Resulted local hyperthermia is known to induce apoptotic cell death in many tissues and has been shown to increase local control and overall cancer survival in combination with radiotherapy and chemotherapy in randomised clinical trials.

Further, the surface 515b may include a SiN surface which can be selectively functionalized with established hydroxamic acid chemistry to attach a drug 670 such as cancer markers, DNA/RNA apatmers, or antigen/antibody for targeted binding of the drug 670.

Further, the surface 515a may include a silicon surface which can be functionalized with a drug 680 which is different from drug 670. Silicon is biodegradable and, therefore, can serve as a slow drug delivery platform with drug 680 loaded on the silicon surface with the help of surface chemistry.

Further, silicon nuclei in silicon particles can be used for magnetic resonance imaging. Natural physical properties of silicon provide surface electronic states for dynamic nuclear polarization, extremely long depolarization times, insensitivity to the in vivo environment or particle tumbling.

As a conclusion, in a single pharmaceutical 600, it can selectively bind to cancer cells (functionaliztion on SiN surface 515b), provide in vivo MRI image (via the silicon in the nanoparticle 550), slowly release drugs to cancer cells locally (drugs loaded on the silicon surface 515a, and silicon slowly dissolve in physiological conditions) to perform chemotheraphy, and allow the thermal therapy to be performed at the same time by use of the gold surface 515c.

With its unique and novel features, the present invention provides a nanoparticle and a method of forming a nanoparticle, which may provide a more uniform nanoparticle than in conventional nanoparticles and methods of forming nanoparticles.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive method and system is not limited to that disclosed herein but may be modified within the spirit and scope of the present invention.

Further, Applicant's intent is to encompass the equivalents of all claim elements, and no amendment to any claim the present application should be construed as a disclaimer of any interest in or right to an equivalent of any element or feature of the amended claim.

The invention claimed is:

1. A method of forming a nanoparticle, comprising:
   forming a layer of semiconductor material on a substrate;
   forming a first layer on the semiconductor material, the first layer having a functionality different from a functionality of the semiconductor material;
   patterning the layer of semiconductor material to form a pillar of the semiconductor material;
   a first etch to form a plurality of strips of the semiconductor material;
   a second etch to divide the plurality of strips into a plurality of pillars of the semiconductor material; and
   separating the pillar from the substrate to form the nanoparticle.

2. The method of claim 1, wherein the substrate comprises a semiconductor-on-insulator (SOI) substrate including a buried oxide layer, and the layer of semiconductor material is formed on the buried oxide layer.

3. The method of claim 2, wherein the separating of the pillar from the substrate comprises undercutting the buried oxide layer by etching the buried oxide layer.

4. The method of claim 1, wherein the semiconductor material comprises one of silicon and germanium.

5. The method of claim 1, further comprising:
   forming a second layer on the semiconductor material, the second layer having a functionality different from the functionality of the semiconductor material, and different from the functionality of the first layer.

6. The method of claim 1, wherein the second layer is different from the first layer in at least one of a bonding property, an energy absorption property and a biodegradability property.

7. The method of claim 1, wherein the forming of the second layer is performed between the first etch and the second etch, so that the second layer is formed on two faces of the nanoparticle.

8. The method of claim 1, wherein the forming of the second layer is performed after the second etch, so that the second layer is formed on four faces of the nanoparticle.

9. The method of claim 1, wherein the first layer comprises an insulator layer and the second layer comprises a metal layer.

10. The method of claim 1, wherein the insulator layer comprises a silicon nitride layer and the metal layer comprises a gold layer.

11. A method of forming a nanoparticle, comprising:
    forming a layer of semiconductor material on a buried oxide layer of a semiconductor-on-insulator (SOI) substrate;
    forming a first layer on the semiconductor material, the first layer having a functionality different from a functionality of the semiconductor material;
    patterning the layer of semiconductor material to form a pillar of the semiconductor material, the patterning of the layer of semiconductor material comprising:
       a first etch to form a plurality of strips of the semiconductor material; and
       a second etch to divide the plurality of strips into a plurality of pillars of the semiconductor material; and
    etching the buried oxide layer to separate the pillar from the buried oxide layer to form the nanoparticle.

12. The method of claim 11, further comprising:
    forming a second layer on the semiconductor material, the second layer having a functionality different from the functionality of the semiconductor material, and different from the functionality of the first layer,
    wherein the second layer is different from the first layer in at least one of a bonding property, an energy absorption property and a biodegradability property.

13. The method of claim 1, wherein the separating of the pillar comprises etching the substrate.

14. The method of claim 1, wherein the substrate comprises an oxide layer, and the separating of the pillar comprises etching the oxide layer.

* * * * *